United States Patent [19]

Deem

[11] 4,102,930

[45] Jul. 25, 1978

[54] ALDOL REACTIONS CATALYZED BY ALKYLENE OXIDE-SALT COMPLEXES

[75] Inventor: Mary Lease Deem, Bernardsville, N.J.

[73] Assignee: Union Carbide Corporation, New York, N.Y.

[21] Appl. No.: 685,542

[22] Filed: May 12, 1976

[51] Int. Cl.² .................. C07C 49/04; C07C 49/08
[52] U.S. Cl. .................. 260/593 R; 260/586 C; 260/601 R; 260/606
[58] Field of Search ............... 260/602, 601 R, 586 C, 260/593 R

[56] References Cited

U.S. PATENT DOCUMENTS

| | | | |
|---|---|---|---|
| 2,660,609 | 11/1953 | Robeson | 260/601 R |
| 2,704,298 | 3/1955 | Bellringer et al. | 260/602 |
| 2,818,443 | 12/1957 | Robeson | 260/602 |
| 2,863,878 | 12/1958 | Lynn | 260/602 |

*Primary Examiner*—James O. Thomas, Jr.
*Assistant Examiner*—Werren B. Lone
*Attorney, Agent, or Firm*—Bernard Francis Crowe

[57] ABSTRACT

Bases generated by the interaction of alkylene oxides and salts provide metal-free catalysis of the aldol reaction. No added solvent is required.

16 Claims, No Drawings

ALDOL REACTIONS CATALYZED BY ALKYLENE OXIDE-SALT COMPLEXES

BACKGROUND OF THE INVENTION

This invention relates to aldol reactions of organic carbonyl compounds and more particularly to the use of catalysts prepared by the interaction of alkylene oxides with salts.

Reactions between electron-accepting reactants, such as aldehydes or ketones, and an active methylene group α-substituted by electron-donating components have been catalyzed commercially by alkali metal hydroxides for some time. For example, 2-ethylhexanediol-1, 3,2-ethylhexanol-1, diacetone alcohol, isophorone, mesityl oxide, methyl isoamyl ketone, and the like have been so-produced followed by, in some cases, dehydration and hydrogenation. The products available from such reaction sequences have been used for insect repellants, organic solvents, plasticizers, detergents, tranquilizers, and the like. While the aldol technology itself is old, various technical problems have persisted over the years. Among these problems may be mentioned process water and solvent costs, separation of the product phases (i.e., water and the condensation compound formed), loss of reactor volume due to solvent/diluent requirements, conversion of starting materials to by-products and contamination of plant-water effluents by the metallic catalysts employed to effect the condensation reaction.

SUMMARY OF THE INVENTION

It now has been found that the condensation of organic carbonyl compounds via an aldol reaction may be effected without the disadvantages outlined above by employing at a temperature of about 30° C. or higher a catalytic amount of a complex of (a) an alkylene oxide, most particularly a 1,2-alkylene oxide and (b) a salt having the formula MZ, where M and Z are most desirably monovalent ions. In some cases species MZ is more effective when used in association with a nonionic surfactant, such as Tergitol NPX (polyethoxylated nonyl phenol).

Representative 1,2-alkylene oxides include ethylene oxide, 1,2-propylene oxide, 1,2-butylene oxide, styrene oxide, and the like. For the salt component (MZ) of the catalysts of this invention cations M include inorganic ions such as those from alkali metals or those of substituted organic onium, ammonium, arsenonium, phosphonium, and the like compounds. For an ammonium ion, having the formula:

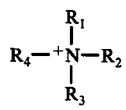

each of $R_1$, $R_2$, $R_3$ and $R_4$ is an alkyl group having 1 to about 18 carbon atoms. These substituents may also contain aromatic moieties. Anion Z is selected from the group consisting of halides (including $F^-$, $Cl^-$, $Br^-$ and $I^-$) and carboxylates having 1 to about 4 carbon aotms including formates, acetates, propionates and butyrates. Larger carboxylate ions are not necessary. Sulfonates and salts of other acids also are monovalent anions which can be used.

The proportions of alkylene oxide to salt are not critical. However, it is preferred to employ nearly stoichiometric quantities of 1,2-alkylene oxide to salt. It is emphasized that only catalytic amounts of the alkylene oxide and salt are required, as neither is incorporated into the desired aldol or dehydro-aldol product. Although not wishing to be bound by any theory or mechanism, it is believed that the catalytic effect of this combination is due to the generation in situ of a discrete alkoxide carbanion by the interaction of the alkylene oxide with the salt anion. For example, as in:

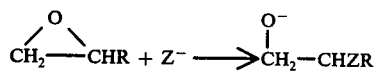

The efficacy of this alkylene oxide/salt catalyst exceeded that of sodium ethoxide in the reaction system.

The term organic carbonyl compounds, used in this invention, includes both aldehydes and ketones. These can be saturated or unsaturated aliphatic compounds and can be substituted as long as an α-hydrogen is present in the acceptor compound. Exemplary aliphatic aldehydes include formaldehyde (plus another carbonyl compound since it can act only as a donor), acetaldehyde, propionaldehyde, butyraldehyde, valeraldehyde, dodecanal, octadecanal, 2-ethylhex-2-enal, crotonal, hex-2-enal, 2-ethylbut-2-enal, vinylcrotonal, 2-methylpropanal, and the like.

Exemplary cycloaliphatic aldehydes include cyclohex-3-enyl aldehyde.

Representative aliphatic ketones include acetone, methyl ethyl ketone, dibutyl ketones, methyl isobutyl ketone, methyl isoamyl ketone, mesityl oxide, 2-methylnon-5-en-4-one, and the like.

No solvent is required for use in these aldol reactions. However, if desired, one will employ organic hydrocarbons having five to twelve or more atoms such as pentane, decane, hexane, and the like. Aqueous organic mixtures can be used if desired. However, the use of solvent-free systems has afforded aldol condensations at conversions of about 94% and efficiencies of about 99–100%.

Pressure is not narrowly critical. The gaseous alkylene oxides used make it preferable to conduct the catalyst preparation at slightly elevated pressures.

Reaction time is not critical but a minimum of about 30 minutes to about 4 hours is preferred. For the manufacture of an α,β-unsaturated carbonyl product (dehydro-aldol) there is no maximum temperature since prolonged exposure does not degrade the product.

The invention is further described in the examples which follow. All parts and percentages are by weight unless otherwise specified.

EXAMPLE 1-CONDENSATION OF n-BUTYRALDEHYDE USING A PROPYLENE OXIDE-TETRAETHYLAMMONIUM BROMIDE CATALYST

An agitated 300 ml. pressure reactor was charged with 60 ml. (49 g., 0.68 mol.) of redistilled n-butyraldehyde and 4.05 × 10⁻³ mol. (0.85 g.) of tetraethylammonium bromide. The mixture was sealed and flushed with nitrogen for 2 to 5 minutes. Ethylene oxide (0.5 ml.; 0.44 g.; 0.01 mol.) was charged to the reactor and the temperature raised to 125° C. for 4 hours. No sudden exotherms or pressure changes were observed during this period. The reactor was cooled to room temperature and flushed with nitrogen to remove any residual ethylene oxide. The reaction mixture was transferred to a graduate to measure the volume of water which had formed. The addition of 20 ml. of glacial acetic acid converted the reaction mixture to a homogeneous phase.

The reaction mixtures were analyzed using a Hewlett-Packard 5710A gas chromatograph equipped with a Hewlett-Packard 3373B integrator and a flame ionization detector. The chromatographic column was a stainless steel tube ⅛ inch × 2 meters loaded with 10% Carbowax 20 M (Trademark of Union Carbide Corporation for polyethylene glycol having a formula molecular weight range of 18,000 to 19,000) on Chromosorb T (a polytetrafluoroethylene support sold by Johns-Manville Co.). The column was used at 150° C. for 8 minutes and then heated to 220° C. at a temperature rate increase of 8°/minute. Representative helium, hydrogen and air flows were 40, 15, and 23 psi respectively.

The conversion of n-butyraldehyde to 2-ethylhex-2-enal and water was 94 and 95%, respectively, with some recovery of unreacted n-butyraldehyde.

CONTROL A

When Example 1 was repeated at a reaction temperature of 30° C. using propylene oxide:tetraethylammonium bromide:butyraldehyde = 0.032:0.059:1 in moles, there was no conversion to 2-ethylhex-2-enal after 2 hours and 100% of the n-butyraldehyde was recovered. Under these mild conditions a higher catalyst ratio (0.094:0.059:1 = propylene oxide:tetraethylammonium bromide:n-butyraldehyde) caused formation of 0.2% 2-ethylhex-2-enal after a one hour reaction interval.

CONTROL B

Example 1 was repeated with the exception that sodium ethoxide (0.28 g.; 4.05 mmol.) was used in place of tetraethylammonium bromide. Analysis of the products indicated 2-ethylhex-2-enal (45 ± 5%) and n-butyraldehyde (57 ± 5%). Some water also was formed.

EXAMPLE 2-ALDOL CONDENSATION OF ACETONE WITH n-BUTYRALDEHYDE USING AN ETHYLENE OXIDE-TETRAETHYLAMMONIUM BROMIDE CATALYST

Example 1 was repeated with the exception that 75 ml. (1.02 mol.) of acetone was used as the carbonyl component in conjunction with 17.7 ml. (24.5 g.; 0.34 mol.) of n-butyraldehyde, 0.84 g. (4.0 mmol.) of tetraethylammonium bromide and 0.5 ml. (0.44 g.; 0.10 mol.) of ethylene oxide. Addition of 20 ml. of acetic acid solubilized the product mixture. Analysis of the products indicated 2-ethylhex-2-enal (74%), n-butyraldehyde (9%), mesityl oxide (5%), acetone (91%), hept-3-en-2-one (3%) and 2-ethyl-3-methylbut-2-enal (0.6%).

EXAMPLE 3-ALDOL CONDENSATION OF n-BUTYRALDEHYDE USING AN ETHYLENE OXIDE/CESIUM IODINE CATALYST

Example 1 was repeated with the exception that cesium iodide (1.05 g.; 4.05 mmol.) was used as the salt (MZ) component of the catalyst combination. Product analysis indicated 2-ethylhex-2-enal (62 ± 5%) and n-butyraldehyde (44 ± 55%). Some water also was formed.

EXAMPLE 4-ALDOL CONDENSATION OF n-BUTYRALDEHYDE USING A PROPYLENE OXIDE/TETRAETHYLAMMONIUM BROMIDE CATALYST

Example 1 was repeated with the exception that propylene oxide (0.58 g.; 0.010 mmol.) was used as the alkylene oxide component of the catalyst combination. Product analysis indicated 2-ethylhex-2-enal (40%) and n-butyraldehyde (55%). Some water also was formed.

Although the invention has been described in its preferred forms with a certain degree of particularity, it is understood that the present disclosure of the preferred forms has been made only by way of Example and that numerous changes may be resorted to without departing from the spirit and scope of the invention.

What is claimed is:

1. Method of condensing organic carbonyl compounds, selected from the group consisting of aliphatic aldehydes and ketones, in an aldol reaction which comprises contacting said carbonyl compounds in the absence of a solvent at a temperature of about 30° to about 125° C. with a catalytic amount of a complex of (a) an alkylene oxide having 2 or more carbon atoms and (b) a salt or a salt plus an oligomeric derivative of ethylene oxide, said salt having the formula MZ wherein M is a cation selected from the group consisting of alkali metal, substituted organic onium, ammonium, arsenonium, and phosphonium cations, where the ammonium cation has the formula:

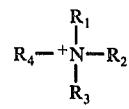

wherein each of $R_1$, $R_2$, $R_3$ and $R_4$ is an alkyl group having 1 to about 18 carbon atoms, and wherein Z is an anion selected from the group consisting of halides, carboxylates having 1 to about 4 carbon atoms, and sulfonates.

2. Method claimed in claim 1 wherein the salt is a quaternary ammonium salt having the formula:

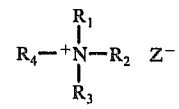

wherein each of $R_1$, $R_2$, $R_3$ and $R_4$ is an alkyl group having 1 to about 18 carbon atoms and Z is an anion selected from the group consisting of halides and carboxylates having 1 or more carbon atoms.

3. Method claimed in claim 1 wherein the salt is cesium iodide.

4. Method claimed in claim 1 wherein the salt is lithium bromide.

5. Method claimed in claim 1 wherein the alkylene oxide is ethylene oxide.

6. Method claimed in claim 1 wherein the alkylene oxide is propylene oxide.

7. Method claimed in claim 2 wherein $R_1$, $R_2$, $R_3$ and $R_4$ are either butyl or ethyl.

8. Method claimed in claim 2 wherein $R_1$ is n-hexadecyl, $R_2$, $R_3$ and $R_4$ are methyl, and Z is bromide.

9. Method claimed in claim 7 wherein Z is bromide, iodide or acetate.

10. Method claimed in claim 1 wherein the organic carbonyl compound is an aldehyde.

11. Method claimed in claim 10 wherein the aldehyde is n-butyraldehyde.

12. Method claimed in claim 10 wherein the aldehyde is acetaldehyde.

13. Method claimed in claim 1 wherein the organic carbonyl compound is a ketone.

14. Method claimed in claim 13 wherein the ketone is acetone.

15. Method claimed in claim 1 wherein the organic carbonyl compounds are a mixture of aldehydes and ketones.

16. Method claimed in claim 15 wherein the aldehyde is n-butyraldehyde and the ketone is acetone.

* * * * *